(12) United States Patent
Buss et al.

(10) Patent No.: US 7,119,228 B2
(45) Date of Patent: Oct. 10, 2006

(54) PROCESS FOR PRODUCING METHIONINE

(75) Inventors: Dieter Buss, Aschaffenburg (DE); Ron Stockfleth, Bonn (DE); Martin Körfer, Kalmthout-Heide (BE); Jürgen Stock, Hanau (DE); Ralf Goedecke, Rodenbach (DE); Hans-Joachim Hasselbach, Gelnhausen (DE); Gundolf Hornung, Wesseling (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/054,424

(22) Filed: Feb. 10, 2005

(65) Prior Publication Data

US 2005/0267314 A1    Dec. 1, 2005

(30) Foreign Application Priority Data

Feb. 14, 2004   (EP)   ................................ 04003353

(51) Int. Cl.
*C07C 51/00*   (2006.01)

(52) U.S. Cl. .................................................... 562/599
(58) Field of Classification Search .................... None
See application file for complete search history.

(56) References Cited

U.S. PATENT DOCUMENTS

| 4,069,251 A | 1/1978 | Mannsfeld et al. ...... 260/534 S |
| 4,303,621 A | 12/1981 | Lussling et al. ............ 423/189 |

FOREIGN PATENT DOCUMENTS

| EP | 0 839 804 | 1/2002 |
| EP | 1 312 611 | 5/2003 |

*Primary Examiner*—Paul A. Zucker
(74) *Attorney, Agent, or Firm*—Michael A. Sanzo; Fitch, Even, Tabin & Flannery

(57) ABSTRACT

The present invention is directed to an improved process for producing methionine in which the by-product methionyl-methionine is quickly converted to the product methionine by a hydrolysis reaction. The process is performed at high temperatures (200° C. to 280° C.) and short residence times (20 s to 200 s) and results in an improved yield of end product methionine.

20 Claims, 1 Drawing Sheet

PROCESS FOR PRODUCING METHIONINE

CROSS REFERENCE TO RELATED APPLICATIONS

The present application claims priority to European application EP 04 003 353.2, filed on Feb. 14, 2004, the contents of which is hereby incorporated by reference.

FIELD OF THE INVENTION

The present invention is directed to a process for the rapid hydrolysis of the dipeptide methionyl-methionine. The hydrolysis reaction may be carried out in connection with a process for producing methionine.

BACKGROUND OF THE INVENTION

Processes for producing methionine are well known in the art and are described in, e.g., U.S. Pat. No. 4,069,251, incorporated herein by reference. One of the most prominent side products of such processes is the dipeptide, methionyl-methionine. The hydrolysis of this dipeptide should result in a higher yield of the final product. However, this reaction is subject to various difficulties. One main problem is that by-products of the hydrolysis may interfere with the carbonization reaction taking place during the final step of methionine formation.

According to EP 1 312 611, proteins are degraded to peptides and/or amino acids in supercritical water (that is at a temperature above 355° C. and at a pressure of at least 22 MPa) or high-pressure hot water near the critical point. However, at such high temperatures, highly corrosion resistant and, hence expensive, equipment is necessary and the end product methionine would be subject to thermal degradation (see EP 839 804). These problems can be avoided by carrying out reactions at a lower temperature but the cleavage of methionyl-methionine typically occurs too slowly at temperatures below 200° C. to be desirable for an industrial process.

Thus, there is a need to provide an economically viable process for hydrolyzing methionyl-methionine at reasonable rates while, at the same time, avoiding undesirable side reactions, the degradation of the end product and the need for highly corrosion-resistant materials.

SUMMARY OF THE INVENTION

The present invention is based upon the discovery that the hydrolysis of methionyl-methionine can be carried out with significantly higher space-time yields (i.e., at low reaction volumes) by a process which comprises the steps of:

a) adding at least one compound selected from potassium carbonate, potassium bicarbonate and potassium hydroxide to a solution containing 5-(β-methylmercaptoethyl)hydantoin to hydrolyze the 5-(β-methylmercaptoethyl) hydantoin and obtain a solution containing methionine, b) saturating the solution containing methionine produced in step a) with carbon dioxide to precipitate the methionine, and separating the precipitate from the remaining solution, i.e., from the "first filtrate,"

c) dividing the first filtrate into a first part and a second part, returning the first part to step (a), and transferring the second part to step (d), d) heating the second part of the first filtrate to a temperature above 200° C. for a time sufficient to obtain a heat-treated filtrate, saturating the heat-treated filtrate with carbon dioxide to precipitate the methionine and potassium bicarbonate, and then separating the precipitated methionine and potassium bicarbonate while leaving a "second filtrate" behind, and e) discharging the second filtrate or returning it to step (a).

This process results in significantly higher space-time yields and improved economic efficiency.

DETAILED DESCRIPTION OF THE INVENTION

Figure 1:
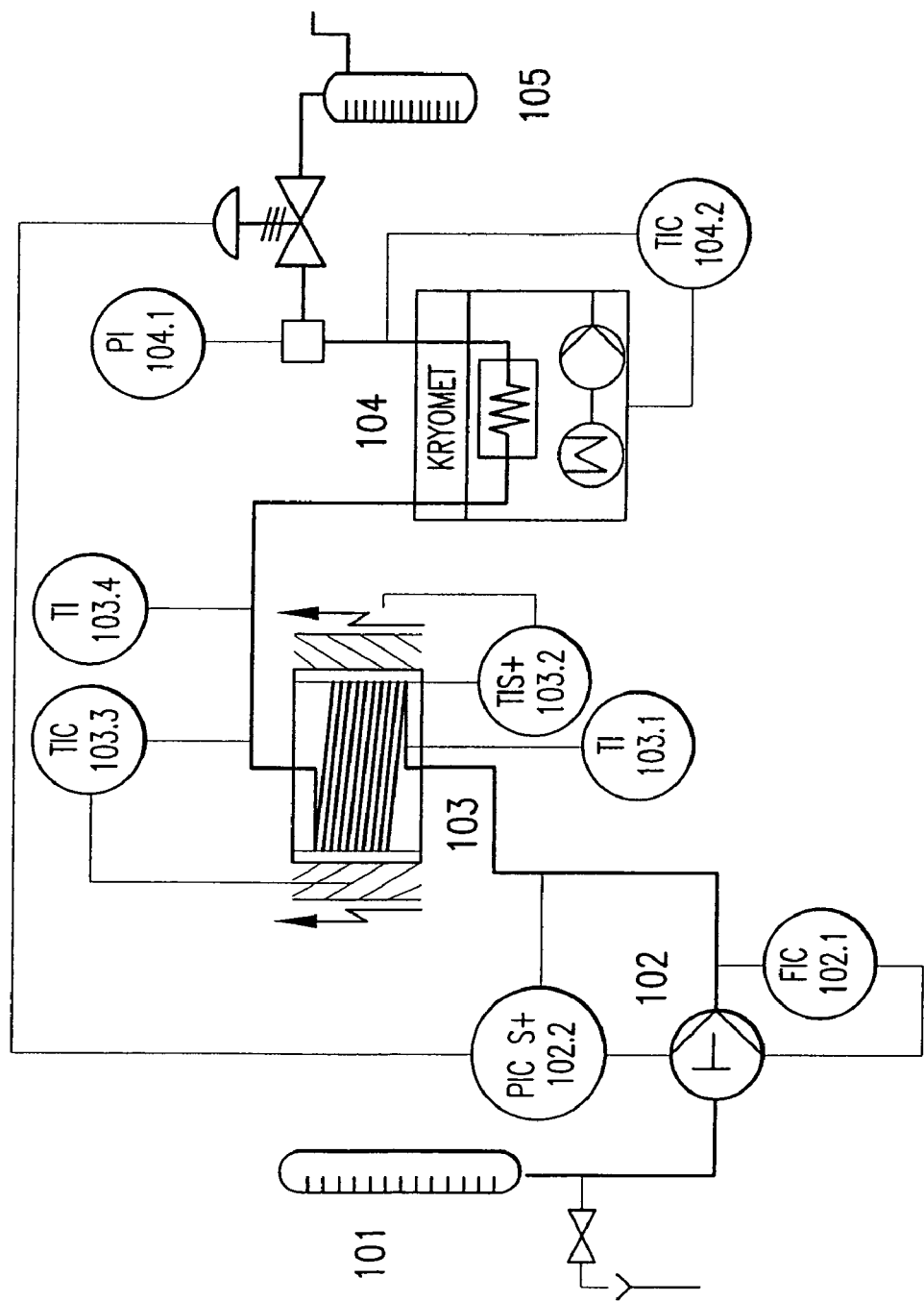
FIG. 1 shows a flow chart of a laboratory facility for carrying the process embodiment described in Example 1.

The present invention is directed to a process for producing methionine which comprises a first step, a) in which 5-(β-methylmercaptoethyl)hydantoin is hydrolyzed using potassium carbonate, potassium bicarbonate, potassium hydroxide or mixtures thereof, and a second step, b) in which the methionine thereby generated is precipitated out of the reaction liquid under carbon dioxide pressure, and collected.

A broad range of conditions may be used for steps (a) and (b) and guidance is provided by methods known in the art (see U.S. Pat. Nos. 4,069,251 and 4,303,621). For example, 5-(β-methylmercaptoethyl)hydantoin may be hydrolyzed using potassium carbonate and/or potassium bicarbonate, at a ratio between the hydantoin and the alkali (potassium carbonate and/or potassium bicarbonate) of between 1:1 and 1:5, and at a temperature of from 120° C. to 220° C. Similar conditions may be employed when using potassium hydroxide or mixtures of potassium hydroxide, potassium carbonate and/or potassium bicarbonate. Carbon dioxide is then fed into the reaction system to saturate the methionine-containing solution and precipitate methionine. This precipitate may be collected using conventional methods of solid-liquid separation, e.g., by filtration.

A first portion of the material remaining in solution after the removal of precipitate in step b), i.e., a first portion of the first filtrate, can be returned to the reaction of step a) either directly or after it is concentrated and a second portion is passed on to step d). Recycling all the filtrate back into step a) over a long period would result in the accumulation of impurities and decomposition products in the system, and would ultimately reduce the purity of the methionine produced. Therefore, a portion of the first filtrate is removed at each step (so-called partial purging) and is passed on to step d).

The second portion of the first filtrate is heated in step d). A second precipitation is then performed using carbon dioxide in the same manner as before. The material left in solution after this second precipitation, i.e., the second filtrate, can either be returned to step a), or can be discarded.

The amount of the filtrate to be purged (second part of the first filtrate in step c)) is not critical and may vary depending on the amount of impurities and colored substances contained in the first filtrate. However, it is preferably about 3–20%, and more preferably 3–10% of the total amount of the first part of the first filtrate. The same percentages apply with respect to the recycling of the second filtrate. The second part of the first filtrate can be heat-treated as it is or after it is concentrated. The filtrate to be heat-treated usually contains about 90–160 g/l of potassium, about 30–100 μl of methionine and about 5–60 g/l of methionyl-methionine. The concentration of potassium referred to may be determined by titration.

The temperature of the heat treatment (step d)) of the second part of the first filtrate is particularly critical and preferably falls within an approximate range of 200° C.–280° C., more preferably within a range of 210° C.–280° C., still more preferably within a range of 220° C.–280° C., and most preferably within the range of 220° C.–260° C.

The dimer is rapidly hydrolyzed at a temperature higher than 200° C., for a time period short enough to prevent the thermal degradation of methionine. Thus, the period of time for heat treatment is also critical and will vary depending upon the concentration of methionine dimer in the second part of the first filtrate. It is preferably less than about 200 seconds (s), more preferably within a range of 20 s to 200 s, still more preferably within a range of 20 s to 150 s, more preferably within a range of about 20 s to about 100 s, and most preferably within a range of about 20 s to about 60 s. Periods significantly longer than 200 s will lead to the thermal degradation of methionine.

It should further be noted, that step d) should be carried out at a pressure above the vapor pressure of the water at the temperature employed. The pressure of carbon dioxide gas to be applied, in terms of gauge pressure (the amount by which the total absolute pressure exceeds the ambient atmospheric pressure), is not critical, but should generally range from about 1.5–20 bar, and preferably from 2–6 bar. When the pressure of carbon dioxide gas is less than about 1.5 bar the recovery of methionine and potassium bicarbonate tend to be poor. In contrast, even when the pressure is increased over about 20 bar, no further improvement in these recoveries is usually observed.

Precipitations are preferably carried out at low temperatures. The temperature, particularly at the time of completion of the precipitation, should preferably fall within the range of −10° C. to +40° C., more preferably within the range of 0° C. to +20° C., and still more preferably within the range of 0° C. to +5° C.

In the present invention, a concentrating operation can be conducted at any step, and is preferably conducted before and/or after the heat treatment of the second part of the first filtrate. The conditions of the concentrating operation are not critical so long as they do not cause substantial thermal degradation of methionine. In order to promote energy efficiency and minimize the corrosion of materials present in reaction equipment, the temperature of the concentrating operation should preferably fall within the range of 50° C. to 160° C., and preferably in the range of 50° C. to 140° C. The pressure of the concentrating operation should preferably fall within the range of 0 to 2 bar in terms of absolute pressure, and more preferably from 0 to 1.5 bar in terms of absolute pressure.

Concentrating operations can be conducted simultaneously with the heat-treating operation in step d). In such a case, the concentrating operation would, of course, be conducted under the operation conditions used in the heat treatment, i.e., above 200° C. for a time period of less than 200 s. However, it would not be advantageous from the viewpoint of energy efficiency and other factors to use the relatively severe conditions present during heat treatment for the purpose of a concentrating operation. Therefore, the concentrating operation and the heat-treating operation are preferably conducted independently of each other.

Treating the second part of the first filtrate in the manner described above removes impurities and colored components present in the reaction system while effectively recovering methionine and potassium bicarbonate contained in the filtrate. Step d) can be conducted either in a batchwise or continuous manner.

As described above, by heat-treating the second part of the first filtrate taken from a conventional process for producing methionine and precipitating methionine out of the heat-treated filtrate under applied pressure of carbon dioxide gas, the methionine dimer present in the system can be hydrolyzed and the resulting methionine recovered. As a result, the yield of methionine is improved, the accumulation of impurities and colored substances in the reaction system is avoided, and methionine and potassium bicarbonate can be recovered easily and with good efficiency. Thus, the present invention is of industrial value.

The process described herein not only increases the yield of the final end product methionine, but, due to significantly shorter reaction times (residence times of from about 20 s to 200 s), the facilities consisting of special materials can be constructed smaller, making the process more economical. It should also be noted, that the hydrolysis (step d)) of the present invention can be carried out without the addition of a solvent. Furthermore, the hydrolysis can be carried out directly with the methionine-mother liquor as starting material. The reaction is catalyzed by either acid or base. For example, suitable catalysis can be achieved by adding KOH to adjust the pH to value about 14. Within the preferred temperature and pressure ranges, unwanted side products are generally avoided.

The invention is described in detail below with reference to Examples, but the invention is not limited thereto.

EXAMPLES

Example 1

The exemplified process may be understood by reference to FIG. 1, in which the reference numbers shown have the following meanings:

101: glass container;
102: HPLC pump;
103: coiled tubing reactor;
104: cryostat device;
105: washing bottle.

Reactant solution is drawn from glass container (101) by an HPLC pump (102) with volume flow being regulated by the number of rotations of the pump (FIC 102.1). The pressure at the pressure side of the pump is regulated by a pressure control valve (PIC S+ 102.2) and an interlock (S+) stops the pump if the pressure exceeds 40 MPa.

The starting mixture flows via a 3×1 mm capillary into the coiled tubing reactor (103). This tubing reactor consists of 6 m of capillary of 3×1 mm, wrapped in a tube with an outer diameter of 168 mm filled with isolation material. The capillary inside this tube has a heat sleeve with a nominal power of 2 kW. In the hot section between the wrapped capillary and the heat sleeve there are two thermocouples (TI 103.1 and 103.2), one of which serves as an overtemperature safety device (TI S+ 103.2).

Downstream, the reactor has a T-piece in which a thermocouple is screwed in (TIC 103.3), thereby allowing the temperature of the solution at the outlet of the reactor (103) to be measured. Based upon this measurement the temperature is controlled using another thermocouple (TI 103.4) found at the outlet of the reactor. Subsequently, the capillary passes through a cryostat device, in which the product solution is cooled to about 50° C.

The pressure of the system is shown by a pressure gauge downstream of the cryostat device (PI 104.1). The solution is expelled from a pressure control valve and collected by an empty washing bottle 105.

Using the system shown in FIG. 1, a mother liquor with a composition of 4.25 mass-% of methionine, 3.36 mass-% of methionyl-methionine and 17.8 mass-% of potassium achieves the conversion rates of methionyl-methionine listed in Table 1, conversion rate being defined as:

$$\text{conversion} = \frac{[\text{met} - \text{met}]_{in} - [\text{met} - \text{met}]_{out}}{[\text{met} - \text{met}]_{in}}.$$

where [met-met] is the concentration of methionyl-methionine at the inlet and outlet of the system as denoted by the subscripts.

TABLE 1

Conversion Rates for Example 1

| Temperature [° C.] | Residence time [s] | Conversion [%] |
| --- | --- | --- |
| 223 | 24 | 21 |
| 223 | 24 | 29 |
| 223 | 32 | 34 |
| 223 | 39 | 38 |
| 239 | 18 | 38 |
| 239 | 24 | 40 |
| 239 | 31 | 47 |
| 239 | 38 | 58 |
| 239 | 60 | 63 |
| 239 | 107 | 77 |
| 239 | 157 | 83 |
| 254 | 18 | 48 |
| 254 | 23 | 62 |
| 254 | 30 | 64 |
| 254 | 37 | 75 |

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for producing methionine, comprising:
   a) adding at least one compound selected from the group consisting of potassium carbonate; potassium bicarbonate; and potassium hydroxide; to a solution containing 5-(β-methylmercaptoethyl)hydantoin to hydrolyze said 5-(β-methylmercaptoethyl)hydantoin and to thereby obtain a solution containing methionine;
   b) saturating the solution containing methionine of step a) with carbon dioxide to precipitate the methionine, and separating the precipitated methionine from a first filtrate;
   c) dividing said first filtrate into a first part and a second part, returning the first part to the reaction of step a), and transferring the second part to step (d);
   d) heating the second part of the first filtrate to a temperature above 200° C. for a period of time and at a pressure sufficient to obtain a heat-treated filtrate, saturating the heat-treated filtrate with carbon dioxide to precipitate the methionine and potassium bicarbonate, and separating the precipitated methionine and potassium bicarbonate from a second filtrate; and
   e) either discarding the second filtrate or returning it to the reaction of step a).

2. The process of claim 1, wherein step d) is carried out at a temperature of from 200° C. to 280° C. for less than 200 seconds.

3. The process of either claim 1 or 2, wherein said temperature is from 210° C. to 280° C.

4. The process of either claim 1 or 2, wherein the temperature is from 220° C. to 280° C.

5. The process of either claim 1 or 2, wherein said temperature is from 220° C. to 260° C.

6. The process of either claim 1 or 2, wherein the residence time for the heat treatment of step d) is between 20 and 200 s.

7. The process of claim 6, wherein said residence time is between 20 and 100 s.

8. The process of either claim 1 or claim 2, wherein step d) is carried out at a pressure above the vapor pressure of water at the temperature employed.

9. The process of either claim 1 or 2, wherein the material in step d) is the methionine-mother liquor.

10. The process of either claim 1 or claim 2, wherein step d) is carried out in the absence of added solvent.

11. The process of claim 1, wherein the molar ratio between the 5-(β-methylmercaptoethyl)hydantoin and sum of said potassium carbonate, potassium bicarbonate and potassium hydroxide is between 1:1 and 1:5.

12. The process of claim 11, wherein step d) is carried out at a temperature of from 200° C. to 280° C. for less than 200 seconds and at a gauge pressure of 1.5–20 bar.

13. The process of either claim 11 or 12, wherein step d) is carried out in the absence of added solvent.

14. The process of claim 13, wherein said temperature is from 210° C. to 280° C.

15. The process of claim 13, wherein the temperature is from 220° C. to 280° C.

16. The process of claim 13, wherein said temperature is from 220° C. to 260° C.

17. The process of claim 11 or 12, wherein the residence time for the heat treatment of step d) is between 20 and 200 s.

18. The process of claim 17, wherein said residence time is between 20 and 100 s.

19. The process of claim 18, wherein step d) is carried out in the absence of added solvent.

20. The process of claim of claim 19 where at least a portion said second filtrate is returned to the reaction of step a).

* * * * *